US007205103B2

(12) United States Patent
Emerson

(10) Patent No.: US 7,205,103 B2
(45) Date of Patent: Apr. 17, 2007

(54) METHOD OF REGULATING TRANSCRIPTION IN A CELL

(75) Inventor: Beverly M. Emerson, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 09/781,592

(22) Filed: Feb. 12, 2001

(65) Prior Publication Data

US 2002/0022021 A1    Feb. 21, 2002

Related U.S. Application Data

(60) Provisional application No. 60/181,864, filed on Feb. 11, 2000.

(51) Int. Cl.
*C12Q 1/68* (2006.01)
*G01N 33/53* (2006.01)
*C07H 21/02* (2006.01)
*C07H 21/04* (2006.01)
*C07K 2/00* (2006.01)

(52) U.S. Cl. .................. 435/6; 536/23.1; 536/24.1; 530/300; 435/7.1

(58) Field of Classification Search ............. 514/2, 514/44; 424/93.2, 9.2; 435/5, 6, 91.1; 536/23.1, 536/24.5, 350
See application file for complete search history.

(56) References Cited

U.S. PATENT DOCUMENTS 5,972,608 A * 10/1999 Peterson et al. .............. 435/6
6,465,629 B1 * 10/2002 Wong et al. ............... 536/23.1

FOREIGN PATENT DOCUMENTS

| EP | 0976825    | 2/2000  |
| WO | WO-98/54311 | 12/1998 |
| WO | WO-99/55891 | 11/1999 |

OTHER PUBLICATIONS

Haswell et al., An in vitro system recapitulates chromatin remodeling at the PHO5 promoter, 1999, Molecular and Cellular Biology, p. 2817-2827.*
Verma et al., Gene therapy- promises, problems adn prospects, 1997, NATURE, vol. 389, pp. 239-242.*
Anderson, Human gene therapy, 1998, NATURE, vol. 392, pp. 25-30.*
Aalfs et al. TIBS, vol. 25, pp. 548-555, 2000.*
Strober et al, Functional Interaction between the hBRM/hBRG1 Transcriptional Activators and the pRB FAmily of Proteins, MCB, 1996, vol. 16, No. 4, pp. 1576-1583.*
Kadonaga, Eukaryotic Transcription: An Interlaced Network of Transcription Factors and Chromatin-Modified Machines, Cell, 1998, vol. 92, pp. 307-313.*

Peterson, Chromatin remodeling enzymes: taming the machines, EMBO, 2002, vol. 3, No. 4, pp. 319-322.*
Wang et al, DNA-binding activity of retinoblastoma prpotein is intrinisic to its carboxyl0-terminal region, Cell Growth and Differentiation, 1990, vol. 1(5), p. 233-239.*
Dahiya et al, Role of LXCXE Binding Site in Rb Functon, MCB, 2000, vol. 20(18), pp. 6799-6805.*
DiRenzo et al, BRG-1 IS Recruited to Estrogen-Responsive Promoters and Cooperates with Factors Involved in Histone Acetylation, MCB, 2000, vol. 20 (20), p. 7541-7549.*
Debril et al, Transcription Factors and Nuclear Receptors Interact with the SWI/SNF Compelx through the BAF60c subunit, JBC, 2004, vol. 2679, No. 16, p. 16677-16686.*
Muchardt and Yaniv, ATP-dependent chroamtin remodelling: SWI/SNF and Co. are on the job, JMB, 1999, vol. 293, p. 187-198.*
Wallberg et a, Recruitement of the SWI/SNF Chromatin Remodeling Complex as a Mechanism of Gene Activation by the Glucocorticoid Receptor t1 Activation Domain, MCB, 2000, vol. 20(6), p. 2004-2013.*
Armstrong, J.A., et al., "A SWI/SNF—Related Chromatin Remodeling Complex, E-RC1, Is Required for Tissue-Specific Transcriptional Regulation by EKLF In Vitro", *Cell*, 95, pp. 93-104, (Oct. 1998).
Armstrong, J.A., et al., "Transcription of chromatin: these are complex times", *Curr. Opin. Genet. Dev.*, 8, pp. 165-172, (1998).
Bagga, R., et al., "Role of Cromatin Structure and Distal Enhancers in Tissue-specific Transcriptional Regulation In Vitro", *Cold Spring Harbor Symposia on Quantitive Biology*, vol. LXIII, Cold Spring Harbor Laboratory Press, pp. 569-576, (1998).
Biggar, S.R., et al., "Continous and widespread roles for the Swi-Snf complex in transcription", *The EMBO Journal*, 18 (8), pp. 2254-2264, (1999).
Burns, L.G., et al., "The Yeast SWI-SNF Complex Facilitates Binding of a Transcriptional Activator to Nucleosomal Sites In Vivo", *Molecular and Cellular Biology*, 17 (8), pp. 4811-4819, (Aug. 1997).
Cairns, B.R., et al., "RSC, an Essential, Abundant Cromatin-Remodeling Complex", *Cell*, 87, pp. 1249-1260, (Dec. 27, 1996).
Cook, T., et al., "Sp1 and Its Likes: Biochemical and Functional Predictions for a Growing Family of Zinc Finger Transcription Factors", *Annals of the New York Academy of Sciences, Vol. 880, Cell and Molecular Biology of Pancreatic Carcinoma—Recent Developments in Research and Experimental Therapy*, J.M. Lohr, et al., Eds., pp. 94-102, (1999).
Cosma, M.P., et al., "Ordered Recruitment of Transcription and Chromatin Remodeling Factors to a Cell Cycle- and Developmentally Regulated Promoter", *Cell*, 97, pp. 299-311, (Apr. 30, 1999).
Davie, J.R., "Covalent modifications of histones: expression from chromatin templates", *Current Opinion in Genetics & Development*, 8 (2), pp. 173-178, (Apr. 1998).

(Continued)

*Primary Examiner*—Scott D. Priebe
*Assistant Examiner*—Maria Marvich
(74) *Attorney, Agent, or Firm*—Klarquist Sparkman, LLP

(57) ABSTRACT

The present invention provides methods and compounds for altering remodeling of chromatin in a cell.

14 Claims, 6 Drawing Sheets

OTHER PUBLICATIONS

Dunaief, J.L., et al., "The Retinoblastoma Protein and BRG1 Form a Complex and Cooperate to Induce Cell Cycle Arrest", *Cell*, 79, pp. 119-130, (Oct. 7, 1994).

Farrants, A.O., et al., "Glucocorticoid Receptor-Glucocorticoid Response Element Binding Stimulates Nucleosome Disruption by the SWI/SNF Complex", *Molecular and Cellular Biology*, 17 (2), pp. 895-905, (Feb. 1997).

Forrester, W.C., et al., "A deletion of the human Beta-globin locus activation region causes a major alteration in chromatin structure and replication across the entire Beta-globin locus", *Genes & Development*, 4 (10), pp. 1637-1649, (1990).

Fryer, C.J., et al., "Chromatin remodelling by the glucocorticoid receptor requires the BRG1 complex", *Nature*, 393, pp. 88-91, (May 1998).

Georgel, P.T., et al., "Role of histone tails in nucleosome remodeling by Drosphila NURF", *The EMBO Journal*, 16 (15), pp. 4717-4726, (1997).

Imbalzano, A.N., et al., "Facilitated binding of TATA-binding protein to nucleosomal DNA", *Nature*, 370, pp. 481-485, (Aug. 11, 1994).

Jacobs, G., et al., "Zinc Finger Gene Database", *The New Biologist*, 2 (6), pp. 583-584, (Jun. 1990).

Jacobs, G.H., et al., "Determination of the base recognition position of zinc fingers from sequence analysis", *The EMBO Journal*, 11 (12), pp. 4507-4517, (1992).

Kadonaga, J.T., "Eukaryotic Transcription: An Interlaced Network of Transcription Factors and Chromatin-Modifying Machines", *Cell*, 92, pp. 307-313, (Feb. 6, 1998).

Kingston, R.E., et al., "ATP-dependent remodeling and acetylation as regulators of chromatin fluidity", *Genes & Development*, 13 (18), pp. 2339-2352, (1999).

Klug, A., "Zinc Finger Peptides for the Regulation of Gene Expression", *Journal of Molecular Biology*, 293 (2), pp. 215-218, (1999).

Klug, A., et al., "'Zinc fingers': A novel protein motif gor necleic acid recognition", *Trends in Biochemical Sciences*, 12, pp. 464-469, (1987).

Kwon, H., et al., "Nucleosome disruption and enhancement of activator binding by a human SW1/SNF complex", *Nature*, 370, pp. 477-481, (Aug. 11, 1994).

Laurent, B.C., et al., "Functional interdependence of the yeast SNF2, SNF5, and SNF6 proteins in transcriptional activation", *PNAS*, 88, 2687-2691, (Apr. 1991).

Martinez-Balbas, M.A., et al., "Drosphila NURF-55, a WD repeat protein involved in histone metabolism", *PNAS*, 95, pp. 132-137, (Jan. 1998).

Mizuguchi, G., et al., "Role of Nucleosome Remodeling Factor NURF in Transcriptional Activation of Chromatin", *Molecular Cell*, 1, pp. 141-150, (Dec. 1997).

Muchardt, C., et al., "ATP-dependent chromatin remodeling: SWI/SNF and Co. are on the job", *Journal of Molecular Biology*, 293, pp. 187-198, (1999).

Neely, K.E., et al., "Activation Domain-Mediated Targeting of the SWI/SNF Complex to Promoters Stimulates Transcription from Nucleosome Arrays", *Molecular Cell*, 4, pp. 649-655, (Oct. 1999).

O'Neill, D., et al., "Tissue-specific and developmental stage-specific DNA binding by a mammalian SWI/SNF complex associated withhuman fetal-to-adult globin gene switching", *PNAS*, 96, pp. 349-354, (Jan. 1999).

Orphanides, G., et al., "FACT, a Factor that Facilitates Transcript Elongation through Nucleosomes", *Cell*, 92, pp. 105-16, (Jan. 9, 1998).

Owen-Hughes, T., et al., "Persistent Site-Specific Remodeling of a Nucleosome Array by Transient Action of the SWI/SNF Complex", *Science*, 273, pp. 513-516, (Jul. 29, 1996).

Paranjape, S.M., et al., "Role of Chromatin Structure in the Regulation of Transcription by RNA Polymerase II", *Annu. Rev. Biochem.*, 63, pp. 265-297, (1994).

Pazin, M.J., et al., "ATP-Dependent Nucleosome Reconfiguration and Transcriptional Activation from Preassembled Chromatin Templates", *Science*, 266, pp. 2007-2011, (Dec. 23, 1994).

Phelan, M.L., et al., "Reconstituition of a Core Chromatin Remodeling Complex from SWI,SNF Subunits", *Molecular Cell*, 3, pp. 247-253, (Feb. 1999).

Smith, J., et al., "A detailed study of the substrate specificity of a chimeric restriction enzyme", *Nucleic Acids Research*, 27 (2), pp. 674-681, (1999).

Sudarsanam, P., et al., "The nucleosome remodeling complex, Snf/Swi, is required for the maintenance of transcription in vivo and is partially redundant with the histone acetyltransferase, Gcn5", *The EMBO Journal*, 18 (11), pp. 3101-3106, (1999).

Utley, R.T., et al., "SWI/SNF Stimualtes the Formation of Disparate Activator-Nucleosome Complexes but Is Partially Redundant with Cooperative Binding", *The Journal of Biological Chemistry*, 272 (19), pp. 12642-12649, (1997).

Utley, R.T., et al., "Transcriptional activators direct histone acetyltransferase complexes to nucleosomes", *Nature*, 394, pp. 498-502, (Jul. 30, 1998).

Wang, W., et al., "Diversity and Specialization of mammalian SWI/SNF complexes", *Genes & Development*, 10, pp. 2117-2130, (1996).

Winston, F., et al., "Yeast SNF/SWI transcriptional activators and the SPT/SIN chromatin connection", *Trends in Genetics*, pp. 387-391, (Nov. 1992).

Yoshinaga, S.K., et al., "Roles of SIW1, SWI2, and SIW3 Proteins for Transcriptional Enhancement of Steriod Receptors", *Science*, 258, pp. 1598-1604, (Dec. 4, 1992).

Yudkovsky, N., et al., "Recruitment of the SWI/SNF chromatin remodeling complex by transcriptional activators", *Genes & Development*, 13, pp. 2369-2374, (1999).

Zhao, K., et al., "Rapid and Phosphoinositol-Dependent Binding of the SWI/SNF-like BAF Complex to Chromatin after T Lymphocyte Receptor Signaling", *Cell*, 95, pp. 625-636, (Nov. 25, 1998).

Cho, H., et al., "A Human RNA polymerase II Complex containing factors that modify chromatin structure", *Molecular and Cellular Biology*, 18(9), (1998), pp. 5355-5363.

Ichinose, H., et al., "Ligand-dependent interaction between the estrogen receptor and the human homologuesof SWI2/SNF2", *Gene: An Int'l J of Genes & Genomes*, 188, (1997), pp. 95-100.

Kadam, S., et al., "Functional selectivity of recombinant mammalian SWI/SNF subunits", *Genes and Development*, 14(19), (2000), pp. 2441-2451.

Vignali, M., et al., "ATP-dependent chromatin-remodeling complexes", *Molecular and Cellular Biology*, 20(6)m (2000)m pp. 1899-1910.

\* cited by examiner

METHOD OF REGULATING TRANSCRIPTION IN A CELL

CROSS-REFERENCE TO RELATED APPLICATIONS

This application is a continuation-in-part of U.S. Provisional Patent Application No. 60/181,864, filed on Feb. 11, 2000, the specification of which is herein incorporated by reference.

The invention was made with the support of NIH Grant No. GM-38760. The U.S. government has certain rights in the invention.

BACKGROUND OF THE INVENTION

Appropriate differentiation and development of higher organisms require precisely regulated expression of multiple genes. The primary control for most genes is exerted at the level of transcription. This involves the combinatorial action of tissue-specific and ubiquitous transcription factors acting at regulatory sequences that are proximal (promoters) or distal (enhancers, insulators, silencers, and locus control regions [LCRs]) to a gene. The existence of functionally distinct cis-acting elements indicates that the high degree of regulation involved in coordinated gene expression within a complex organism requires more intricate circuitry than a simple promoter can provide to turn genes on and off. A critical aspect of this circuitry and coordination is the regulation imposed upon genes within a complex nuclear environment.

The human genome, however, is composed of about $3.3 \times 10^9$ bp. If stretched out, this would represent a length of more than 1.8 meters of DNA. The cell nucleus that contains two copies of this DNA is, on the other hand, a sphere of no more than 6 µm in diameter. To reach this high level of compaction, human DNA is, like in all other eukaryotes, organized into chromatin. The packaging of DNA into chromatin within the eukaryotic nucleus is highly organized and plays a critical role in regulating gene expression and other nuclear processes. The basic structural unit of chromatin is the nucleosome, which consists of ~146 bp of DNA wrapped in 1.75 superhelical turns around a histone octamer containing two molecules each of histones H2A, H2B, H3 and H4. This unit is repeated once every 200+/−40 bp as a nucleosomal array in chromosomal DNA. The array is further compacted into a higher-order structure by the association of histone H1 with nucleosomes within the array.

The functional consequence of chromatin packaging, in general, is to restrict access of the DNA to a variety of DNA-binding proteins that regulate gene activity. Biochemical and genetic evidence amply demonstrate that nucleosomes are normally repressive for transcription. Several elegant mechanisms have evolved, however, that modulate chromatin structure to increase the accessibility of DNA for protein interaction. These pathways involve distinct protein complexes that function either as motors to disrupt nucleosomes (ATP-driven chromatin remodeling complexes) or as enzymatic machinery to chemically modify histones (histone acetyltransferases and deacetylases). Such mechanisms may be critical in programming genes to be either active or inactive in a particular cell type or to be poised for expression at a specific stage of development or in response to environmental signals.

Chromatin structural changes can occur at several levels: either globally by the decondensation (active nucleic acids) or condensation (inactive nucleic acids) of a large chromosomal domain or locally by the disruption (active) or formation (inactive) of one or more nucleosomes on a promoter or enhancer region. Global chromatin structural changes have been shown to occur in the human β-globin gene locus by the action of the distal LCR (Forrester, W. C. et al., *Genes Dev.*, 4, 1637 (1990)). In addition, active genes are characterized by containing hyperacetylated histones and undermethylated DNA. Interestingly, both global and local levels of chromatin structural perturbation often require the interaction of regulatory proteins with histone amino-terminal tails within the nucleosome, which are also the main targets of post-translational modification (for review, see Davie, J. R., *Curr. Opin. Nucleic Genet. Dev.*, 8, 173 (1998)). Two critical pathways that facilitate this interaction involve distinct protein complexes that function either as motors to disrupt nucleosomes (ATP-driven chromatin remodeling complexes) or as enzymatic machinery to modify histones chemically and alter their affinity for DNA (histone acetylases, HATs/deacetylases, HDACs/kinases).

The mechanisms by which specific genes are activated in chromatin have been extensively investigated in a variety of biochemical and genetic systems. Paranjape, S. M. et al., *Annu. Rev. Biochem.*, 63, 265 (1994). Recent in vitro studies have focused on the role of specific cellular and viral factors in chromatin structural reconfiguration and nucleic acid expression. A common theme to emerge is that chromatin remodeling and transcriptional activation are separate processes that can be regulated by distinct proteins or subunits/domains of a given protein. This was shown originally with the GAL4-VP16 activator using chromatin-assembled genes. Pazin, M. J. et al., *Science*, 266, 2007 (1994). The observation that chromatin accessibility is not sufficient for transcription has important regulatory implications as nucleic acids can be preset by chromatin remodeling to be activated at a later time.

There are seven chromatin remodeling complexes that have been described to date: SWI/SNF, RSC, NURF, CHRAC, ACF, NURD and RSF. All are multi-subunit complexes with molecular weights ranging from 2 MDa to 0.5 MDa. Biochemical analyses have shown that these complexes can disrupt nucleosomal structure in a ATP-dependent manner (all complexes), facilitate factor binding (SWI/SNF, NURF, ACF) and transcription from chromatin-assembled genes (NURF, ACF and RSF). Several properties indicate that these complexes are functionally and mechanistically distinct. For example, RSC is an abundant complex in yeast and is encoded by essential genes, in marked contrast to SWI/SNF (SWI stands for mating type SWItch and SNF for Succrose Non-Fermenting), suggesting a different biological role for these two complexes. Cairns, B. R. et al., *Cell*, 87, 1249 (1996). Furthermore, NURF has recently been shown to facilitate transcriptional activation from preformed chromatin templates in combination with GAL4-HSF. Mizuguchi, G. et al., *Mol. Cell.* 1, 141 (1998). In this assay, NURF cannot be replaced by either yeast SWI/SNF or CHRAC.

A novel complex has recently been described, using a purified in vitro transcription system, that alleviates the nucleosomal block to elongation. Orphanides, G. et al., *Cell*, 92, 105 (1998). This 230 kDa complex, called FACT (facilitates chromatin transcription), appears to function quite distinctly from chromatin remodeling complexes as it does not facilitate transcriptional initiation or require ATP hydrolysis. Thus, promoter-proximal chromatin remodeling is one critical step in gene activation but is not sufficient for transcription unless coupled with activities, such as FACT, which permit efficient elongation through nucleosomes.

Little is known about the manner in which remodeling complexes disrupt nucleosomes. Recent studies demonstrate that the ability of NURF to alter nucleosomal structure is impaired by crosslinking of nucleosomal histones, removal of amino-terminal histone tails, or mutation of lysine residues within the histone H4 tail; this indicates that the flexible tails play a critical role in the remodeling process. Georgel, P. T. et al., *EMBO. J.*, 16, 4717 (1997). The formation of a ternary complex composed of DNA, histones, and activator is facilitated by SWI/SNF, which results in the destabilization but not the loss of nucleosomes and persists after its removal. Owen-Hughes, T. et al., *Science*, 273, 513 (1996). Recent studies demonstrate that the SWI/SNF-dependence of genes regulated by the yeast activator GAL4 is determined by the presence of low, rather than high, affinity GAL4 DNA binding sites on the promoter. The presence of high-affinity sites or a nucleosome-free region can overcome the requirement for this remodeling complex in vivo. Burns, L. G. et al., *Mol. Cell. Biol.*, 17, 4811 (1997).

Interestingly, one subunit of NURF has recently been identified as the WD repeat protein, p55, which is also a subunit of *Drosophila* CAF1 (chromatin assembly factor 1). p55 homologs are found associated with histone acetyltransferases and deacetylases. Thus, many of the diverse chromatin-altering complexes may utilize common subunits. Martinez-Balbas, M. A. et al., *Proc. Natl. Acad. Sci. USA*, 95, 132 (1998).

It is clear that multiple levels of control are involved in regulated nucleic acid expression, from the activation of the chromosomal domain in which a nucleic acid resides to the formation of a basal initiation complex on a given promoter within the domain. Questions remain as to how tissue- or developmental-state-specific expression is established and how coordinate expression of multiple genes is achieved. In addition, the mechanism by which critical DNA control elements, often acting at long-range, such as enhancers, insulators, silencers, and LCRs, regulate transcription is still poorly understood.

Thus, there remains a continuing need for high-throughput screening assays that identify small molecule compounds that enhance or block the association between chromatin remodeling complexes and the specific transcription factors with which they interact, such as the BRG1 subunits of the SWI/SNF complex and proteins containing zinc finger motifs. In this way very specific drugs are developed that modulate the activation or repression of selective nucleic acids that are regulated by SWI/SNF (BRG1) complexes and zinc finger DNA-binding transcription factors. There also remains a need for a method of treating nucleic genetic diseases where nucleic acid expression is targeted in a highly selective manner.

SUMMARY OF THE INVENTION

The present invention provides a method of altering remodeling of chromatin in a cell comprising administering to the cell a compound that modulates an interaction of a subunit of a chromatin remodeling complex and a domain within a protein. The compound modulates the interaction by inhibiting or enhancing the subunit of the chromatin remodeling complex and the domain within the protein. The protein may be a transcription factor. The domain may be a nucleic acid binding domain or an activation domain. The nucleic acid binding domain may be a zinc-finger domain, such as a peptide or an artificial zinc-finger domain. The first peptide may be linked to a second protein to form a fusion protein. The nucleic acid may be DNA or RNA.

The chromatin remodeling complex may be SWI/SNF, RSC, NURF, CHRAC, ACF, NURD and RSF. The remodeling complex may be tissue-specific. In particular the chromatin remodeling complex may be one of the following SWI/SNF subunits: BRG1, BRM, BAF 155, BAF 170, INi1, BAF 60, BAF 47, or BAF 57. The subunit may be associated with at least one other subunit. The SWI/SNF complex may be E-RC1.

In the method of the present invention, the compound may inhibit or enhance the interaction of the chromatin remodeling complex subunit and the domain within the protein.

In the method of the present invention the zinc finger DNA-binding domain may be GATA-1 (erythroid), Sp1 (ubiquitous), EKLF (erythroid), FKLF (fetal), BKLF (basic), GKLF (gut), or LKLF (lung); Wilm's tumor suppressor protein (WT1); BRCA1 or BRCA2; KRAB; a BTB/POZ domain-containing zinc-finger protein, such as PLZF (promyelocytic leukemia zinc finger); or a zinc finger-containing nuclear hormone receptors, such as an androgen, estrogen, thyroid, progesterone, or glucocorticoid receptors; it may be from a regulator of tissue-specific nucleic acid expression.

The chromatin remodeling complex subunit may be from an organism such as a plant or animal, such as a human.

The present invention further provides a method of altering activation of transcription in a cell comprising administering to the cell a compound that modulates the interaction of a subunit of a chromatin remodeling complex and a domain within a protein.

The present invention additionally provides a method of screening for modulating compounds comprising contacting a subunit of a chromatin remodeling complex and a domain within a protein with the modulating compound in the presence of chromatin, and comparing the level of chromatin remodeling or transcription activation in the presence and absence of the compound.

The present invention also provides an in vitro system to increase or decrease transcription comprising a subunit of a chromatin remodeling complex and a domain within a protein.

The present invention also provides a pharmaceutical agent for gene therapy comprising a compound that modulates the interaction of a subunit of a chromatin remodeling complex and a domain within a protein, and a pharmaceutically effective carrier. The compound may modulate the interaction by either inhibiting or enhancing the interaction of the subunit of the chromatin remodeling complex and the domain within the protein. The compound may interact with the subunit of the chromatin remodeling complex or it may interact with the domain within the protein.

The present invention provides a method of altering remodeling of chromatin in a cell comprising administering to the cell a compound that modulates the interaction of a subunit of a chromatin remodeling complex or a domain within a protein with nucleic acid. The nucleic acid may be a regulatory region, such as a promoter, enhancer, insulator, silencer, or locus control regions [LCRs].

DETAILED DESCRIPTION OF THE INVENTION

A gene is made of nucleic acid and packaged into chromosomes (or "chromatin") by associating with small basic histone proteins. All genes are packaged into chromatin structures in the nucleus of cells. Yet many variations in chromatin structure exist and it is the variations that determine whether a gene is active or inactive in a particular cell type (or tissue or organ). For example, a gene that is packaged into a very condensed chromatin structure is inactive, whereas packaging into a loose, extended chromatin structure is characteristic of active genes.

Figure 1:
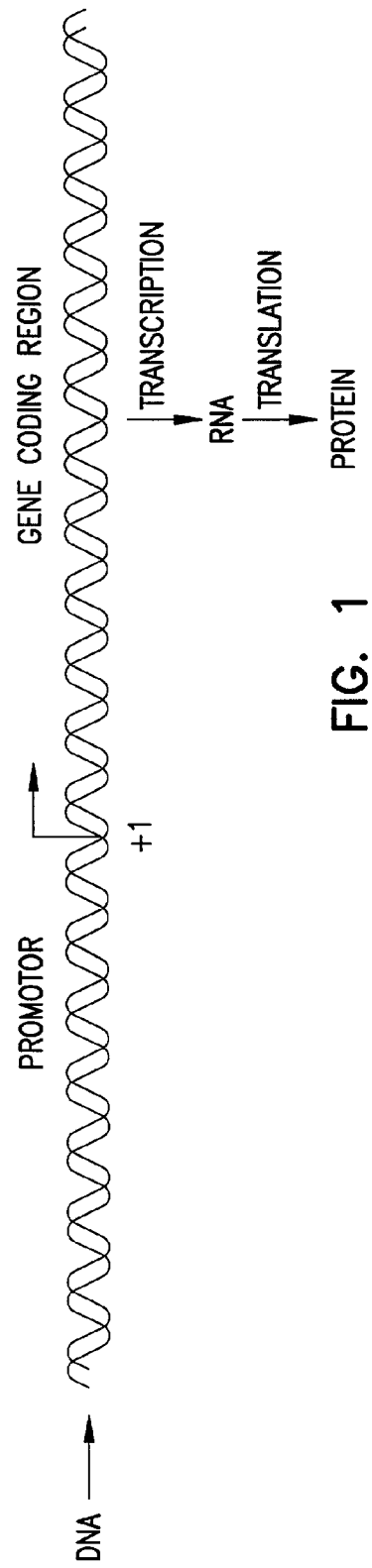
FIG. 1 is a schematic drawing of a typical gene that is controlled by a promoter region located just ahead of the beginning of the coding sequence of the gene.
Figure 2:
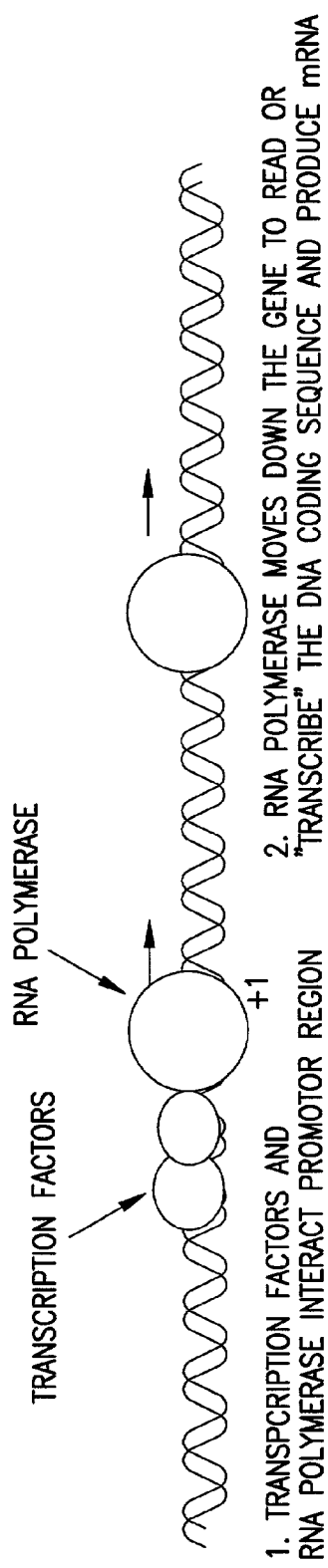
FIG. 2 is a schematic drawing of the interaction of proteins with the promoter DNA to start transcribing the DNA and produce mRNA.
Figure 3:
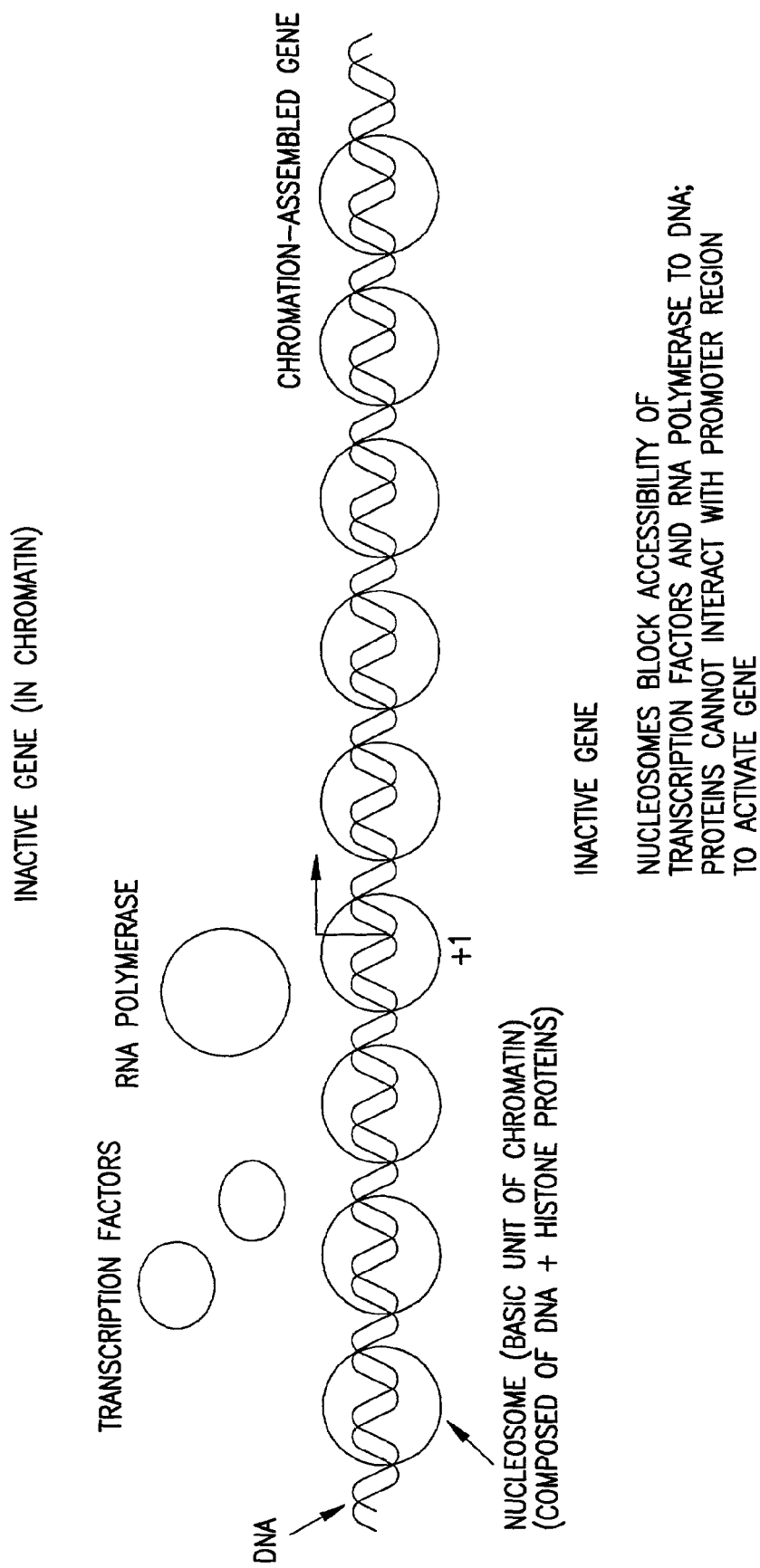
FIG. 3 is a schematic drawing of the interaction of nucleosomes with DNA in inactive DNA, wherein the DNA is wrapped around the nucleosomes by the affinity of negatively-charges DNA for positively-charged histones, which blocks the accessibility of the DNA to the activator proteins and RNA polymerases.

Chromatin structure regulates gene activity by determining whether a gene is accessible to interact with nucleic acid-binding proteins that control its expression. A typical gene is controlled by a promoter region located just ahead of the beginning of the coding sequence of the gene. See FIG. 1. Proteins (such as activators, RNA polymerase, etc.) must interact with the nucleic acid promoter to start reading or transcribing the gene. See FIG. 2. These proteins are called collectively transcription factors. Nucleosomes (or chromatin) impose a barrier to the interaction of transcription factors. If these factors cannot interact with the nucleic acid regulatory region, such as a DNA promoter region, then the nucleic acid cannot be expressed. If the nucleosomal structure is changed in some way to loosen its affinity for the nucleic acid, then transcription factors can interact with the promoter and activate gene expression. See FIG. 3. The ability of chromatin to control gene expression in this manner (by "selective" gene expression) is crucial for the development and health of all organisms. It enables the establishment of body plan and distinct cell types that produce organs that are capable of specialized physiological functions.

Figure 4:
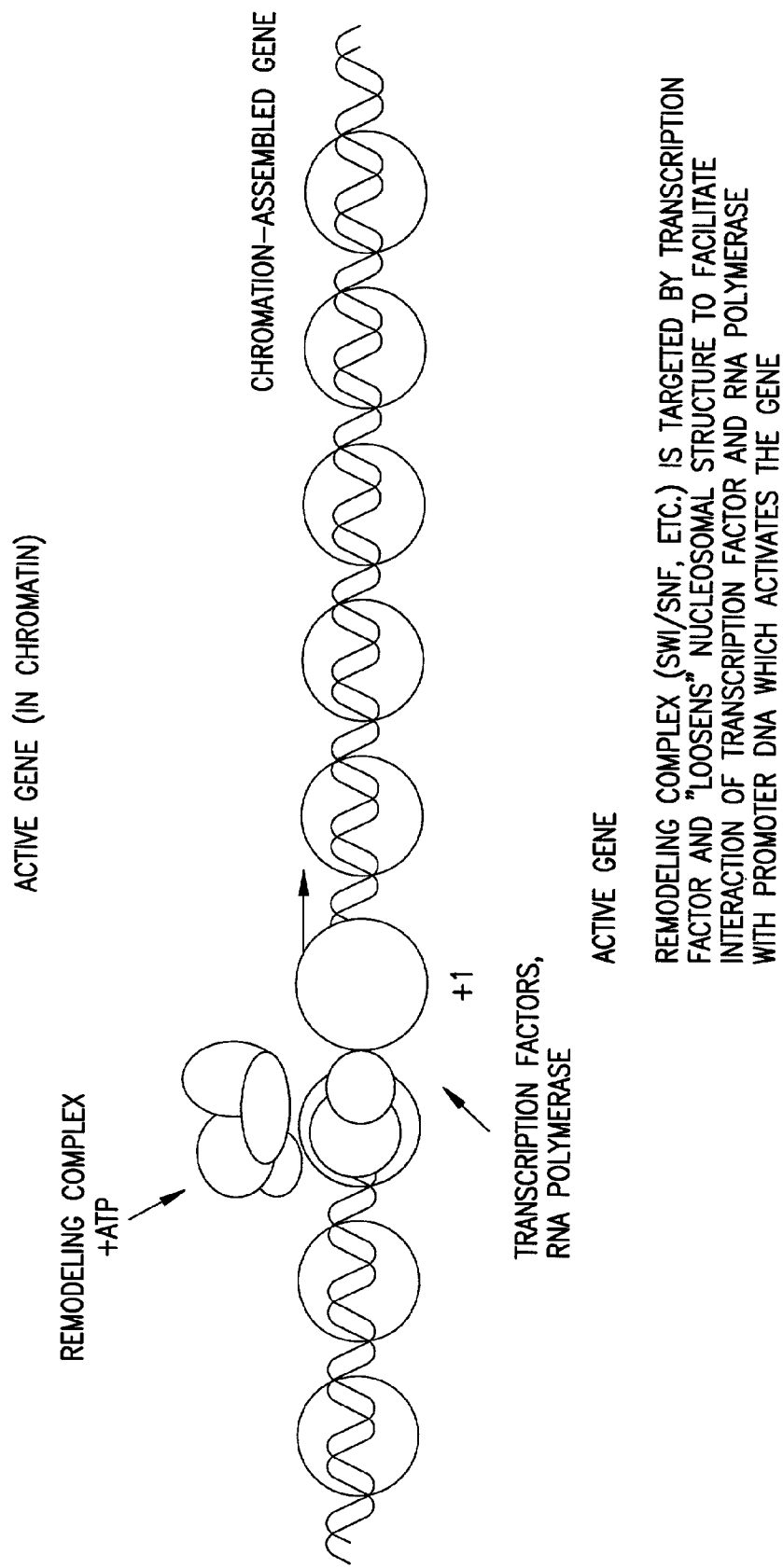
FIG. 4 is a schematic drawing of the interaction of the remodeling complex with the inactive gene. The remodeling complex "loosens" the nucleosomal structure so that activators can bind to the DNA, thereby activating the gene.

Recently, multi-subunit protein complexes have been discovered that modify chromatin structure to be either "decondensed" or "condensed" that results in genes being either active or inactive. These proteins are called "chromatin remodeling complexes." For example, a chromatin remodeling complex can weaken the affinity of DNA for histones to generate a "loose, decondensed" nucleosomal structure. This facilitates the interaction of transcription factors with nucleic acid that can result in gene activation. See FIG. 4. Targeted chromatin remodeling is a critical and required step in gene activation that precedes transcription. These chromatin remodeling complexes are found in a wide variety of life forms, including both plants and animals.

There are seven chromatin remodeling complexes that have been described to date: SWI/SNF, RSC, NURF, CHRAC, ACF, NURD and RSF. The two major families of chromatin remodeling complexes are SWI/SNF and ISWI (imitation switch). Both SWI/SNF and ISWI complexes are composed of multiple protein subunits and distinct family members exist within each class. Examples include BRG1, hBRM, BAF 155, BAF 170, INi1, BAF 60, BAF 47, BAF 57. Thus, chromatin remodeling complexes can be biochemically heterogeneous but all carry out the same basic function of modulating nucleosomal structure. Because all remodeling complexes carry out the same basic function biochemically, the critical question arises of how specificity of gene regulation is achieved by these complexes.

Many zinc finger proteins have been studied to date. For example, there are zinc finger proteins that are regulators of tissue-specific gene expression such GATA-1 (erythroid), Sp1 (ubiquitous), EKLF (erythroid), FKLF (fetal), BKLF (basic), GKLF (gut), LKLF (lung). There are also zinc finger-containing nuclear hormone receptors such as, androgen, estrogen, thyroid, progesterone, glucocorticoid receptors. Another zinc finger-containing protein is Wilm's tumor suppressor protein, WT1. WT1 encodes a zinc finger transcription factor implicated in kidney differentiation and tumorigenesis. It strongly regulates amphiregulin, a member of the epidermal growth factor family, among other genes. BRCA1 and BRCA2 are zinc finger-containing proteins implicated in hereditary breast and ovarian cancers. KRAB repressor domain-containing zinc-finger proteins are involved in epigenetic silencing of genes. BTB/POZ are domain-containing zinc-finger proteins such as, PLZF (promyelocytic leukemia zinc finger), which is fused to RARalpha (retinoic acid receptor alpha) in a subset of acute promyelocytic leukemias (APLs), where it acts as a potent oncogene.

Figure 5:
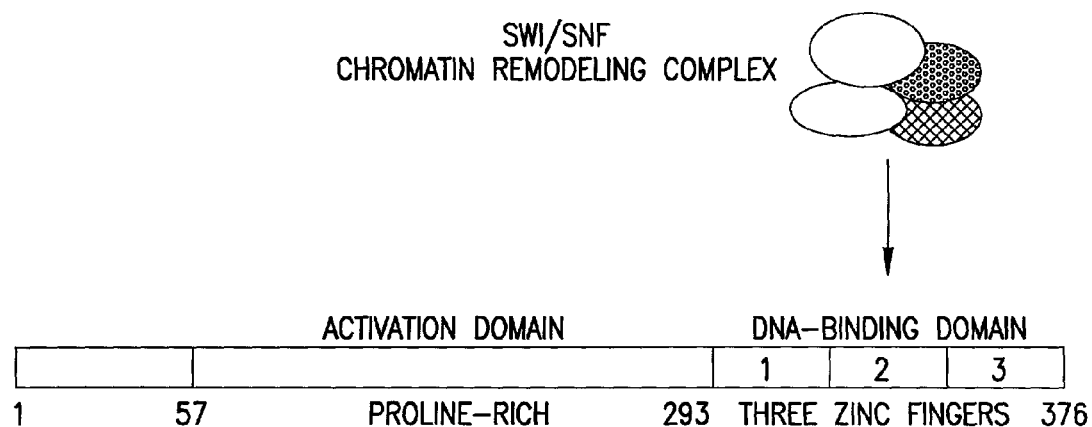
FIG. 5 is a diagram of EKLF protein domains and region of SWI/SNF interaction.

The inventors previously demonstrated that mammalian SWI/SNF can specifically activate distinct chromatin-assembled genes in vitro. (Armstrong et al. (1998) *Cell* 95: 93–104). The inventors have now defined the mechanistic basis for the observed functional specificity of mammalian SWI/SNF complexes (See Example 1 below). The inventors demonstrate that SWI/SNF interacts directly with a particular class of transcription factors that contain zinc finger DNA-binding domains. See FIG. 5. Interaction occurs through the DNA-binding domain rather than the activation domain or other domains of the protein. SWI/SNF fails to activate genes that are regulated by at least two non-zinc finger containing proteins, TFE-3 and NF-κB because it cannot interact with them. Thus, SWI/SNF selectively interacts only with certain proteins, such as zinc-finger containing proteins.

Figure 6:
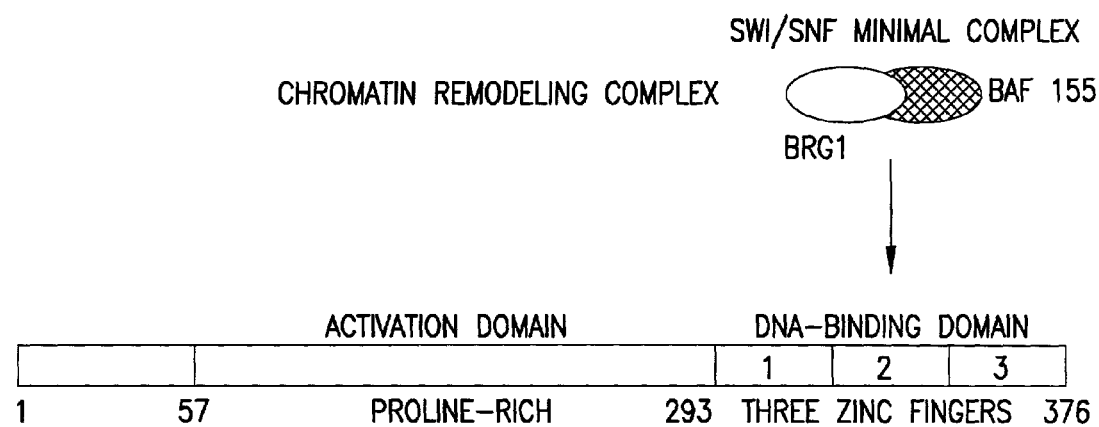
FIG. 6 is an identification of recombinant SWI/SNF subunits that interact with zinc-finger DNA-binding domains to target specific chromatin remodeling.

Using recombinant subunits of mammalian SWI/SNF, the inventors have defined the subunits that interact directly with zinc finger DNA-binding domains as BRG1, BAF 155, and BAF 170. Moreover, the inventors show that a minimal SWI/SNF recombinant complex composed of only BRG1 and BAF 155 is sufficient to activate transcription with a full length zinc finger containing protein, EKLF, (but not with TFE-3 or NF-κB), and that BRG1/BAF 155 plus the zinc finger domain alone are sufficient to "target" chromatin remodeling to specific promoters. See FIG. 6.

Interestingly, mammalian SWI/SNF complexes exist in two broad classes depending upon whether they contain the subunit BRG1 or BRAHMA (BRM) as their DNA-dependent ATPase. Zinc finger DNA-binding domain specificity is achieved only with BRG1-containing SWI/SNF complexes. No transcription or targeted remodeling is observed with zinc finger proteins and recombinant BRM-containing SWI/SNF complexes. BRM complexes presumably interact with another class of transcription factors, possibly through their activation rather than DNA-binding domains. This is very advantageous because it further demonstrates the degree of specificity that chromatin remodeling complexes employ to regulate distinct subsets of genes. Thus, each class of complexes regulates different subsets of genes using distinct mechanisms for gene targeting Based upon these experimental observations, the invention includes assays to screen for compounds that modulate with the ability of a chromatin remodeling complex and a domain within a protein. For example, the chromatin remodeling complex may be a mammalian SWI/SNF-BRG1 complex that interacts with a zinc finger DNA-binding protein. In this way, the regulation of individual or small numbers of genes can be manipulated for therapeutic purposes. This high degree of targeted gene specificity drastically reduces the undesirable side effects of drugs that grossly inhibit gene activation in general, such as drugs that would inhibit the activity of all chromatin remodeling complexes. Suitable zinc finger DNA-binding proteins for use herein include Zif268, GLI, XFin, and the like. See also, Klug and Rhodes, Trends Biochem. Sci., 12:464, 1987; Jacobs and Michaels, New Biol., 2:583, 1990; and Jacobs, EMBO J., 11:4507–4517, 1992.

Chimeric restriction enzymes are a novel class of engineered nucleases in which the non-specific DNA cleavage domain of Fok1 (a type IIS restriction endonuclease) is fused to other DNA-binding motifs. Smith J, et al. *Genes Res. Jan.* 15, 1999; 27(2):674–81. The latter include the three common eukaryotic DNA-binding motifs, namely the helix-turn-helix motif, the zinc finger motif and the basic helix-loop-helix protein containing a leucine zipper motif. Such chimeric nucleases have been shown to make specific cuts in vitro very close to the expected recognition sequences. The most important chimeric nucleases are those based on zinc finger DNA-binding proteins because of their modular structure. Recently, one such chimeric nuclease, Zif-QQR-F(N) was shown to find and cleave its target in vivo. This was tested by microinjection of DNA substrates and the enzyme into frog oocytes (Carroll et al., 1999). The injected enzyme made site-specific double-strand breaks in the targets even after assembly of the DNA into chromatin. In addition, this cleavage activated the target molecules for efficient homologous recombination. Since the recognition specificity of zinc fingers can be manipulated experimentally, chimeric nucleases could be engineered so as to target a specific site within a genome. The availability of such engineered chimeric restriction enzymes should make it feasible to do genome engineering, also commonly referred to as gene therapy.

Many transcription factors contain zinc finger DNA-binding domains that are implicated in human disease. Zinc-Finger Proteins in Oncogenesis : DNA-Binding and Gene Regulation (Annals of the New York Academy of Sciences, Vol 684) by Mel Sluyser (Editor) New York Academy of Sciences; Transcription Factors and Human Disease (Oxford Monographs on Medical Genetics, No 37) Gregg L. Semenza (September 1998) Oxford Univ Press; ISBN: 0195112393; Eukaryotic Transcription Factors David S. Latchman 375 pages 3rd edition (May 1999) Academic Pr; ISBN: 0124371779; Klug A. Zinc finger peptides for the regulation of gene expression. J Mol Biol. Oct. 22, 1999; 293(2):214 . 8; Thiel G, Lietz M, Leichter M. Regulation of neuronal gene expression. Naturwissenschaften. 1999 January 86(1):1–7; Ashraf SI, Ip YT. Transcriptional control: repression by local chromatin modification. Curr Biol. Sep. 24, 1998; 8 (19):R683–6; Bieker J J, Ouyang L, Chen X. Transcriptional factors for specific globin genes. Ann N Y Acad Sci. Jun. 30, 1998; 850:64–9; Takatsuji H. Zinc-finger proteins: the classical zinc finger emerges in contemporary plant science. Plant Mol Biol. 1999 April; 39(6):1073–8; Chandrasegaran S, Smith J. Chimeric restriction enzymes: what is next? Biol Chem. 1999 July–August;380(7–8): 841–8.

Interestingly, these zinc finger domains have different amino acid structures and exist in distinct categories. Further, different structures within these zinc finger domains are recognized by SWI/SNF complexes, such as a BRG1/BAF 155 complex. Thus, different pharmaceutical agents can be administered to interact with very specific structures within a particular zinc finger domain and its binding to a SWI/SNF subunit, and thereby discriminate between different categories of zinc finger-containing proteins. This further enhances the modulation of expression of specific genes for therapeutic purposes while greatly minimizing undesirable side effects.

Compounds that are useful in the present invention include those that modulates (i.e., inhibits or enhances) the interaction of a subunit of a chromatin remodeling complex and a domain within a protein. This modulating activity of the compound could be as a result of the small molecule interacting with the subunit of the chromatin remodeling complex, such as a SWI/SNF subunit, or with the domain within the protein, such as a zinc-finger binding domain. The compounds useful in the present invention are found among biomolecules including, but not limited to, peptides, polypeptides, peptidomimetics, saccharides, fatty acids, steroids, purines, pyrimidines, derivatives, structural analogs or combinations thereof. Alternatively, the compound could be an antibody. Appropriate compounds further include chemical compounds (e.g., small molecules having a molecular weight of more than 50 and less than 5,000 Daltons, such as hormones). Candidate organic compounds comprise functional groups necessary for structural interaction with proteins, particularly hydrogen bonding, and typically include at least an amine, carbonyl, hydroxyl or carboxyl group, preferably at least two of the functional chemical groups. The candidate organic compounds often comprise cyclical carbon or heterocyclic structures and/or aromatic or polyaromatic structures substituted with one or more of the above functional groups. Known pharmacological compounds are candidates which may further be subjected to directed or random chemical modifications, such as acylation, alkylation, esterification, amidification, etc., to produce structural analogs.

Appropriate compounds can additionally be contained in libraries, for example, synthetic or natural compounds in a combinatorial library; a library of insect hormones is but one particular example. Numerous libraries are commercially available or can be readily produced; means for random and directed synthesis of a wide variety of organic compounds and biomolecules, including expression of randomized oligonucleotides and oligopeptides, also are known. Alternatively, libraries of natural compounds in the form of bacterial, fungal, plant and animal extracts are available or can be readily produced. Additionally, natural or synthetically produced libraries and compounds are readily modified through conventional chemical, physical and biochemical means, and may be used to produce combinatorial libraries. Such libraries are useful for the screening of a large number of different compounds.

A variety of other compounds may be included in the method of the present invention. These include agents like salts, neutral proteins, e.g., albumin, detergents, etc. that are used to facilitate optimal protein-protein binding or interactions and/or reduce nonspecific or background binding or interactions. For example, reagents that improve the efficiency of the assay, such as protease inhibitors, nuclease inhibitors, antimicrobial agents, may be used. The mixture of components are added in any order that provides for the requisite modulation. Moreover, such compounds additionally can be modified so as to facilitate their identification or purification. Such modifications are well known to the skilled artisan (e.g., biotin and streptavidin conjugated compounds).

Formulations of Compounds

In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts are obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids also are made.

The compounds may be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The following examples are intended to illustrate but not limit the invention.

EXAMPLE 1

Figure 7A:
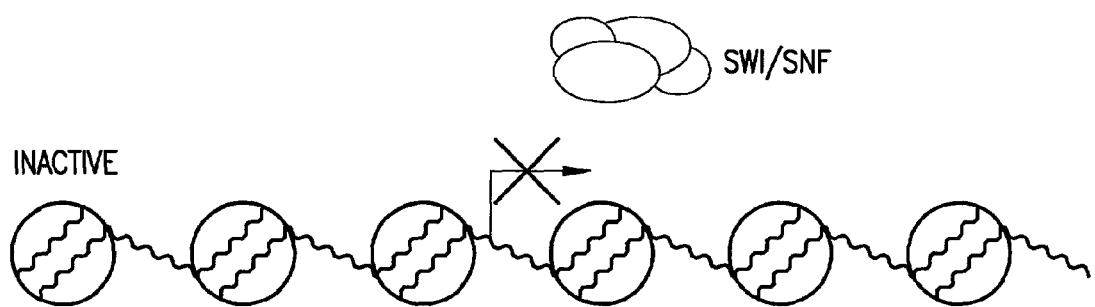
FIG. 7 depicts possible mechanism of SWI/SNF-dependent chromatin remodeling by interaction with zinc-finger DNA binding proteins.
Figure 7B:
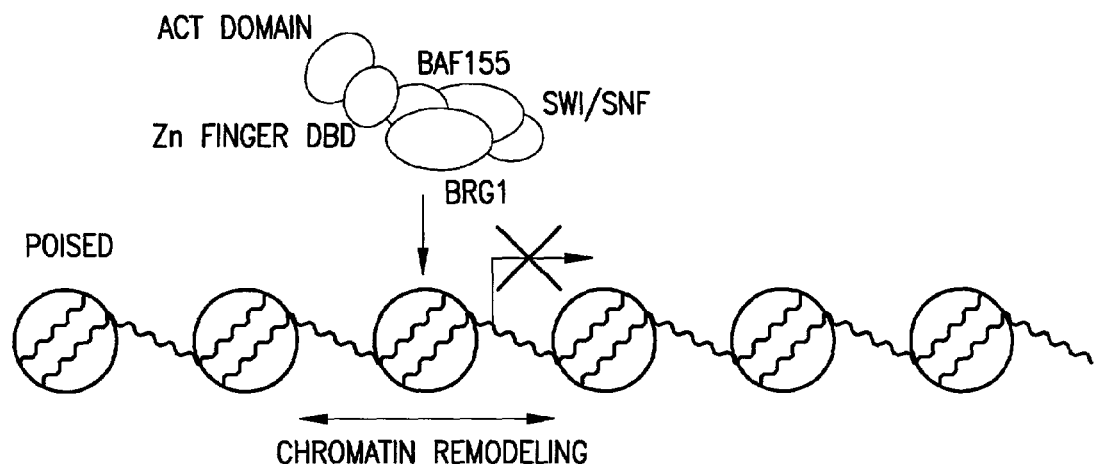
Figure 7C:
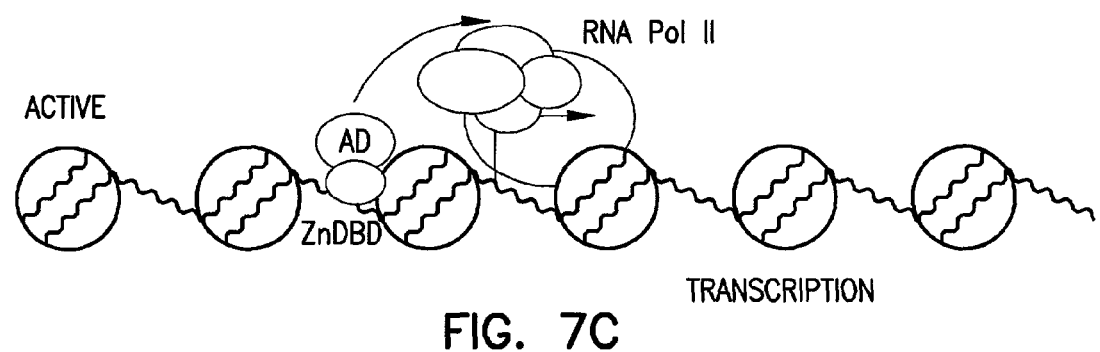

SWI/SNF Specific Regulation of Transcription from Chromatin-Assembled Genes in a Factor-Specific Manner In Vitro The selective expression of genes that have been packaged into repressive chromatin structures is a fundamental process that controls gene regulation during development. Kadonaga, J. T., Cell, 92, 307 (1998); Armstrong, J. A. et al., Curr. Opin. Genet. Dev., 8, 165 (1998). The SWI/SNF family of chromatin remodeling complexes plays a key role in facilitating the binding of specific transcription factors to nucleosomal DNA in diverse organisms from yeast to humans. Kingston, R. E. et al., Genes Dev., 13, 2339 (1999); Wang, W. et al., Genes Dev., 10, 2117 (1996). Yet the process by which SWI/SNF and other chromatin remodeling complexes activate specific subsets of genes is poorly understood. Here it is shown that mammalian SWI/SNF regulates transcription from chromatin-assembled genes in a factor-specific manner in vitro. FIG. 7. The DNA-binding domains of several zinc finger proteins, including EKLF, interact directly with SWI/SNF complexes to generate DNase I hypersensitive sites within the human β-globin promoter in chromatin. Interestingly, it was found that two SWI/SNF subunits (BRG1 and BAF155) are necessary and sufficient for remodeling and transcriptional activation of the β-globin gene promoters by EKLF in vitro. By contrast, the HIV-1 enhancer-binding factors TFE-3 and NF-κB fail to support remodeling or activation by these recombinant SWI/SNF subunits or by the entire native SWI/SNF complex. Thus, the DNA-binding domains of specific transcription factors can differentially target SWI/SNF complexes to chromatin in a gene-selective manner.

The SWI/SNF chromatin remodeling complex has been shown to control hormone-inducible and tissue-specific gene activation and cell proliferation by diverse regulators, including the glucocorticoid receptor (GR), the retinoblastoma protein, and the erythroid-restricted activator of β-globin genes, EKLF. Yoshinaga, S. K. et al., Science, 258, 1598 (1992). Yoshinaga, S. K. et al., Science, 258, 1598 (1992); Muchardt, C. et al., EMBO J., 12, 4279 (1993); Ostlund Farrants A. K. et al., Mol. Cell. Biol., 12, 895 (1997); Fryer, C. J. et al., Nature, 393, 88 (1998); Dunaief, J. L. et al., Cell, 79, 119 (1994); Armstrong, J. A. et al., Cell, 95, 93 (1998); O'Neill, D. et al., Proc. Natl. Acad. Sci. USA, 96, 349 (1999). It was previously demonstrated that transcriptional activation of chromatin-assembled human β-globin genes by EKLF requires a mammalian SWI/SNF complex, termed E-RC1. Armstrong, J. A. et al., Cell, 95, 93 (1998). SWI/SNF facilitates the targeted interaction of EKLF to its binding site at −90 within the β-globin promoter resulting in the generation of a DNase hypersensitive region, indicative of structurally remodeled chromatin. The observation that the HIV-1 enhancer factor TFE-3 was unable to induce transcription in the presence of the E-RC1 complex further suggested that promoter remodeling requires specific DNA-binding proteins in vitro. Armstrong, J. A. et al., Cell, 95, 93 (1998).

SWI/SNF Selectively Functions with Several Zinc Finger DNA-binding Proteins to Remodel Chromatin and Activate Transcription in vitro.

To assess the specificity of chromatin remodeling in vitro, the ability of various DNA-binding proteins to co-operate with SWI/SNF and activate transcription from the chromatin-assembled human β-globin promoter was tested. In vitro transcription of the chromatin-assembled β-globin DNA by transcription factors (EKLF, GATA-1, and Sp-1) in the presence of the E-RC1 (SWI/SNF) chromatin remodeling complex was tested. The plasmid template was assembled into chromatin and incubated in the absence or presence of 580 ng DNA-cellulose E-RC1 (SWI/SNF) fraction and, in some reactions, 37 pmol of recombinant EKLF, either 30, 60 and 150 nmol of an Sp1-containing fraction or 35, 45 or 65 pmol of recombinant GATA-1 per 1 µg chromatin were added. The amount of E-RC1 was estimated as described previously (Armstrong, J. A. et al., *Cell*, 95, 93 (1998)). All proteins were added to assembled chromatin and incubated for 20 min at 27° C. Chromatin assembly and transcription reactions were conducted as described.

The transcription factor Sp1 binds to DNA with the same sequence specificity as EKLF, and recognizes a CACC motif in the β-globin promoter (−90), whereas the GATA-1 factor interacts with two different sites (at −120 and −200) within this region. The E-RC1 (SWI/SNF) complex greatly increases transcription from the β-globin gene in the presence of either EKLF, Sp1, or GATA-1.

Figure 8:
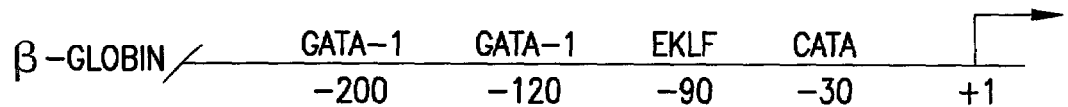
FIG. 8 shows the DNA binding regions of GATA-1, EKLF and TFIID (on CATA box) proteins on the β-globin promoter.

Next, an analysis of the ability of different β-globin gene DNA-binding proteins to generate DNase I hypersensitive sites within the β-globin promoter in the presence or absence of E-RC1 was tested. Assembled chromatin was incubated with E-RC1 and either EKLF, Sp1, or GATA-1 as described above, and half of the reaction was divided into two and digested with 2 and 1 U of DNase I as described (Armstrong, J. A. et al., *Cell*, 95, 93 (1998)). A schematic diagram of the β-globin promoter is shown in FIG. 8. In all cases activation occurred concomitantly with nucleosome structural remodeling as detected by DNase I hypersensitive site formation within the β-globin promoter in reactions analyzed in parallel. Thus, E-RC1 can co-operate with EKLF, Sp1, and GATA-1 to activate β-globin transcription in vitro.

Figure 9:
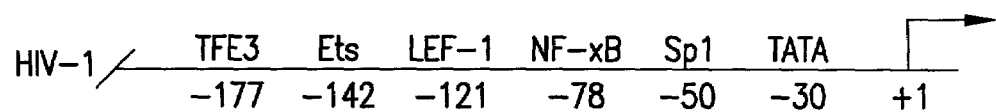
FIG. 9 shows the DNA binding regions of TFE3, Ets, LEF-1, NF-κB, Sp1 and TFIID (on TATA box) proteins on the HIV-1 promoter.

Through its ability to bind to the three Sp1 sites in the HIV-1 promoter, the EKLF protein was also able to induce transcription from the chromatin-assembled HIV-1 promoter in an E-RC1-dependent manner. An aliquot of 100 ng pHIV-1/Luc was assembled into chromatin and either incubated without enhancer factors, or with the following DNA-binding proteins: EKLF; 2 pmol, 3 pmol, or 4 pmol; or TFE-3, 5 pmol. Alternatively, the template was incubated with either 4 pmol EKLF or with 5 pmol TFE-3 during nucleosome assembly. Some reactions also contained 58 ng DNA-cellulose E-RC1 (SWI/SNF), which was always added after nucleosome assembly. A mixture of recombinant TFE-3 (5 pmol) and NF-κB (p50:p65; 1 pmol) was incubated with 100 ng HIV-1 chromatin either before or after nucleosome assembly, and transcription in vitro was analyzed as above in the presence or absence of E-RC1, which was added after nucleosome assembly. Control reactions lacked any enhancer-binding proteins. Transcription from the α-globin gene DNA was included as a control for RNA recovery. A schematic diagram of the HIV-1 promoter is shown in FIG. 9.

EKLF binds weakly to the HIV-1 promoter, however, and was unable to activate transcription when incubated with the template prior to chromatin assembly, indicating that its ability to interact functionally with E-RC1 enhanced its binding affinity for the HIV-1 template. By contrast, the TFE-3 enhancer factor was unable to stimulate transcription when incubated, with the HIV-1 chromatin template in the presence of E-RC1. TFE-3 binds with high affinity to an E-box in the HIV-1 enhancer on naked DNA and can activate transcription strongly when bound to the template prior to chromatin assembly. This suggests that its inability to function with E-RC1 reflects its failure to co-operate with this remodeling complex to recognize its binding site in organized chromatin. Even the combination of TFE-3 and NF-κB, which activates HIV-1 transcription strongly when bound to the template during chromatin assembly, was completely unresponsive to E-RC1 when added to pre-assembled chromatin. Consistent with the restriction to DNA-binding, E-RC1 also failed to generate DNase I hypersensitive site formation by TFE-3 and NF-κB on HIV-1 chromatin. Thus, E-RC1 supports binding and activation of HIV-1 transcription by EKLF, but not by TFE-3 or NF-κB. Thus, the E-RC1 (SWI/SNF) complex displays functional specificity towards different classes of transcription factors in vitro.

The DNA-binding Domain of EKLF is Sufficient to Direct Chromatin Remodeling by E-RC1 (SWI/SNF) in vitro.

To identify the role of distinct EKLF protein domains in SWI/SNF-mediated chromatin remodeling and transcriptional activation of the β-globin gene in the presence of the E-RC1 (SWI/SNF) complex, a series of EKLF mutant proteins were examined in vitro. Assembled chromatin templates were incubated with either wild type or mutant EKLF proteins (37 pmol per 1 µg chromatin) and 580 ng of the DNA-cellulose E-RC1 fraction. Removal of the proline-rich activation domain significantly decreased β-globin transcription relative to the wild-type EKLF protein, and neither the activation domain alone nor the zinc finger DNA-binding domain (DBD) could support β-globin transcription on chromatin.

Figure 10:
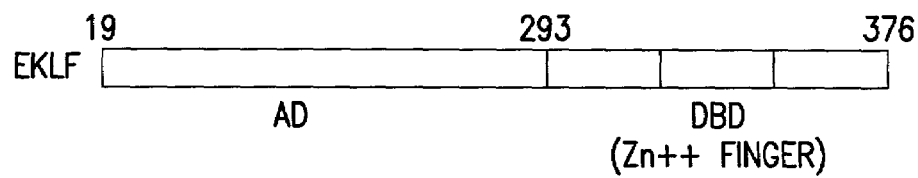
FIG. 10 shows the structure of the EKLF DNA-binding protein.

The ability of different EKLF mutant proteins to generate DNase I hypersensitivity at the β-globin promoter in the presence of the E-RC1 (SWI/SNF) complex in vitro was also analyzed. After assembly, chromatin was incubated with E-RC1 in the presence of either wild type or mutant EKLF protein. A schematic diagram of the domain structure of human EKLF is shown in FIG. 10. The zinc finger DNA-binding domain was as active as full-length EKLF in generating DNase I hypersensitive site formation in the presence of E-RC1. By contrast, the isolated EKLF activation domain had no ability to support remodeling. These data indicate that the DNA-binding domain of EKLF is sufficient to generate specific nucleosome remodeling in the presence of E-RC1, whereas transcriptional activation requires, in addition, the EKLF activation domain.

SWI/SNF Subunits Interact Specifically with the DNA-binding Domain of EKLF and GATA-1.

Next, it was determined whether EKLF targets E-RC1 to the chromatin template through a direct interaction with one or more of the SWI/SNF subunits in the complex. A wealth of data indicate that SWI/SNF can facilitate the binding of diverse transcription factors to chromatin. Kwon, H. et al., *Nature*, 370, 477 (1994); Imbalzano, A. N. et al., *Nature*, 370, 481 (1994); Bums, L. G. et al., *Mol. Cell. Biol.*, 17, 4811 (1997); Utley, R. T. et al., *J. Biol. Chem.*, 272, 12642 (1997). The SWI/SNF complex has been reported to associate directly with the glucocorticoid receptor (GR), the Retinoblastoma tumor suppressor protein (Rb), as well as other factors. Yoshinaga, S. K. et al., *Science*, 258, 1598 (1992); Muchardt, C. et al., *EMBO J.*, 12, 4279 (1993);

Ostlund Farrants A. K. et al., *Mol. Cell. Biol.*, 17, 895 (1997); Fryer, C. J. et al., *Nature*, 393, 88 (1998); Dunaief, J. L. et al., *Cell*, 79, 119 (1994); Yudkovsky, N. et al., *Genes Dev.*, 13, 2369 (1999); Neely, K. E. et al., *Mol. Cell*, 4, 649 (1999). In the case of the GR, this interaction is mediated through the DNA-binding domain, whereas acidic activators have been reported to interact with SWI/SNF subunits through their activation domains. Yoshinaga, S. K. et al., *Science*, 258, 1598 (1992); Muchardt, C. et al., *EMBO J.*, 12, 4279 (1993); Ostlund Farrants A. K. et al., *Mol. Cell. Biol.*, 17, 895 (1997); Yudkovsky, N. et al., *Genes Dev.*, 13, 2369 (1999); Neely, K. E. et al., *Mol. Cell*, 4, 649 (1999).

GST pull-down assays were performed with E-RC1 and 1 μg of GST-fused wild-type or mutant EKLF, GATA-1, TFE-3, NF-κB (DNA-binding domain) and GST proteins bound to glutathione-Sepharose beads. Beads were analyzed for individual SWI/SNF subunits by Western blot analysis as described (Armstrong, J. A. et al., *Cell*, 95, 93 (1998)) using the following antisera: BAF250, BRG1, BAF60a, BAF57, or BAF47. Proteins were expressed and purified as described. Pazin, M. J. et al., *Science*, 266, 2007 (1994); Bieker, J. J. et al., *Mol. Cell. Biol.*, 15, 852 (1995); Hung, H. L. et al., *Mol. Cell. Biol.*, 19, 3496 (1999). Using this combined GST "pulldown" approach and Western blot analysis with a DNA-cellulose enriched E-RC1 fraction, it was found that all of the SWI/SNF (BAF) subunits tightly associate with full-length EKLF, full-length GATA-1 and the zinc finger DNA-binding domains of either EKLF or GATA-1. Interestingly, the isolated EKLF activation domain had no affinity for SWI/SNF, nor did the GATA-1 activation domain.

No interaction was observed between the SWI/SNF (BAF) subunits and NF-κB (p50), whereas only BAF57 subunit displayed any affinity for TFE-3, either full-length or DNA-binding and activation subdomains. The significance of BAF57 interaction with TFE-3 is unclear, and the absence of the remaining BAF subunits indicates that some of the BAF57 may exist as a free subunit in the E-RC1 fraction. The inability of TFE-3 to activate transcription through ERC-1 indicates that interaction with free BAF57 is insufficient to mediate the remodeling necessary to facilitate TFE-3 binding to chromatin.

To assess which SWI/SNF subunits may interact directly with EKLF, a protein overlay ("Far-Western") analysis was performed. The DNA-cellulose E-RC1 fraction was subjected to SDS-PAGE, stained with silver, blotted onto a PVDF membrane, and processed for Far-Western analysis using two different probes: GST-EKLF; followed by anti-EKLF antibody, or $^{32}P$ labeled GST-EKLF. Incubation of EKLF with the DNA-cellulose E-RC1 fraction revealed a strong interaction with the BAF155 subunit, and possibly a weak interaction with the BRG1 and BAF170 subunits. Thus, interactions between the DNA-binding domain of EKLF and SWI/SNF (BAF) subunits in the E-RC1 complex underlie the observed selectivity of chromatin remodeling.

Recombinant SWI/SNF Subunits Confer Selective Transcriptional Activation or Chromatin-assembled Genes.

Previous studies have demonstrated that nucleosome disruption is achieved in vitro with only partial SWI/SNF complexes or with the BRG1 subunit alone, which is a DNA-dependent ATPase. Phelan, M. L. et al., *Mol. Cell*, 3, 247 (1999). Consequently, it was important to determine whether recombinant SWI/SNF subunits can support factor-dependent prompter remodeling and transcriptional activation on chromatin templates in vitro. It was found that recombinant BRG1 and BAF155 are sufficient for transcriptional activation of the chromatin-assembled β-globin gene by EKLF in vitro. Only very weak transcriptional activation of the β-globin promoter was observed when EKLF was incubated in the presence of the free recombinant SWI/SNF subunits, BRG1, BAF155 (the yeast SWI3 homologue), BAF170, or hBRM. Importantly, addition of a minimal SWI/SNF complex containing recombinant BRG1 and BAF155 generated high levels of β-globin transcription by EKLF, which was fully comparable to that obtained with native E-RC1. Assembly of BAF170 into this minimal BRG1/BAF155 complex did not increase transcription relative to the levels observed with BRG1/BAF155 alone.

Although hBRM contains ATPase activity and is able to support general nucleosome remodeling on its own in vitro, neither hBRM nor a hBRM/BAF155 complex was able to activate β-globin gene transcription in the presence of EKLF. Most interestingly, the specificity of transcriptional activation observed with the E-RC1 complex was also recapitulated with the minimal recombinant SWI/SNF complex. In particular, the recombinant BRG1 and BAF155 complex failed to support activation of the chromatin-assembled HIV-1 promoter in the presence of either the TFE-3 or NF-κB (p65) enhancer-binding proteins. Whereas these two proteins are able to activate HIV-1 transcription strongly when incubated with the HIV-1 enhancer during chromatin assembly. Thus, recombinant SWI/SNF subunits do not support transcription from the chromatin-assembled HIV-1 promoter by TFE-3 or NF-κB in vitro. These experiments demonstrate that a minimal SWI/SNF complex, composed of only the BRG1 and BAF155 subunits, is sufficient to recognize the EKLF DNA-binding domain and activate expression from the chromatin-assembled β-globin promoter in a transcription factor-dependent manner in vitro.

An important question about chromatin remodeling by SWI/SNF concerns the strategies that are utilized to regulate specific subsets of genes and respond to signaling pathways, as defined both genetically and biochemically. Winston, F. et al., *Trends Genet.*, 8, 387 (1992); Zhao, K. et al., *Cell*, 95, 625 (1998). Recent studies demonstrate that SWI/SNF complexes are targeted to acidic activator, through interactions with the activation domain, in a manner similar to some models for recruitment of histone acetyltransferase complexes. Yudkovsky, N. et al., *Genes Dev.*, 13, 2369 (1999); Neely, K. E. et al., *Mol. Cell*, 4, 649 (1999); Utley, R. T. et al., *Nature*, 394, 498 (1998). By contrast, the present data indicate that mammalian SWI/SNF complexes can be targeted to selected promoters through direct interaction with specific DNA-binding domains. The present findings support earlier studies showing that the DNA binding domain of the glucocorticoid receptor can function co-operatively with SWI/SNF in transcription. Yoshinaga, S. K. et al., *Science*, 258, 1598 (1992); Muchardt, C. et al., *EMBO J.*, 12, 4279 (1993). In addition, fusion proteins that join SWI/SNF subunits to the LexA DNA-binding domain are able to induce expression from LexA promoter binding sites in yeast, suggesting that SWI/SNF is directed to specific sites by DNA binding domains. Laurent, B. C. et al., *Proc. Natl. Acad. Sci. USA*, 88, 2687 (1991). Because chromatin remodeling can occur in the absence of an activation domain, although transcription itself is abolished, it is reasonable to assume that SWI-SNF facilitates targeted nucleosomal disruption and protein binding through functional interaction with specific DNA-binding domains. Pazin, M. J. et al., *Science*, 266, 2007 (1994); Wong, J. et al., *EMBO*, 16, 3158 (1997). Once a protein is bound to chromatin, however, interactions between transcription factor activation domains and SWI/SNF could further modulate transcription.

Interactions between the SWI/SNF complex and multiple activators may be important for genes in which SWI/SNF is continuously required for transcription beyond the initial remodeling events, particularly in cases where SWI/SNF is involved in subsequent recruitment of transcription factors that are unable to engage remodeling complexes. Biggar, S. R. et al., *EMBO J.*, 18, 2254 (1999); Sudarsanam, P. et al., *EMBO J.* 18, 3101 (1999); Cosma M. P. et al., *Cell*, 97, 299 (1999). The HIV-1 enhancer factors TFE-3 and NF-κB are unable to respond to E-RC1 (or recombinant SWI/SNF) to induce transcription or interact with SWI/SNF through their DNA-binding domains. These proteins either recognize distinct classes of chromatin remodeling complexes or depend upon other enhancer factors to recruit remodeling complexes to the HIV-1 promoter. Thus, targeted nucleosomal remodeling can be achieved by the direct interaction of SWI/SNF with specific classes of DNA-binding domains that is critical for activation of transcription on chromatin in vitro. This degree of specificity requires only two SWI/SNF subunits, BRG1 and BAF155, and may be one critical determinant of selective gene regulation by this diverse family of remodeling complexes.

EXAMPLE 2

Pharmaceutical Screening Protocol

Zinc finger motifs appear to be the most widely used of all types of DNA-binding domains and have been estimated to constitute as much as 1% of the human genome. They are the optimal natural design for DNA targeting because of the modular nature of different zinc finger mini-domains that can function together to achieve DNA binding specificity over a very large number of combinatorial possibilities. Klug, A. J. Mol. Biol. 293: 215–218 (1999). Moreover, DNA binding sites for zinc finger proteins, GC-rich sequences and related GT- or CACC boxes, appear in numerous cellular and viral nucleic acids and control regions.

A large repertoire of zinc finger-containing DNA-binding proteins are known to exist in mammalian cells. Cook, T. et al. Ann. N.Y. Acad. Sci. 880:94–102 (1999). Among these are transcription factors that regulate critical processes such as development, differentiation, and morphogenesis. These factors can function as either transcriptional activators or repressors.

A protocol for an assay of how different drugs are tested to be effective in enhancing or blocking the association between mammalian SWI/SNF subunits and zinc finger motifs is very straightforward in design. First, it is initially determined which SWI/SNF subunits interact with a specific zinc finger domain-containing protein by co-immunoprecipitation analyses. This has already been demonstrated for EKLF-BRG1 complex formation in Example 1 above.

Second, a modified binding assay is devised for high-throughput drug screening by attaching a fluorescent "tag" to one protein, for example recombinant BRG1, and adding this labeled protein to multi-well plates that have been coated with a specific concentration of the full length protein or its zinc finger motif. A "control" (the protein or zinc finger motif containing mutations that abolish SWI/SNF subunit binding as determined in the first step above) is also used to monitor any non-specific binding that may occur in these reactions.

Third, after a brief period of incubation for protein-protein interaction to occur, the stability of these complexes is challenged by screening a library of small molecule compounds for their ability to alter the affinity of zinc finger-SWI/SNF subunit binding.

Fourth, after a period of incubation with these compounds, the multi-well plates is extensively washed with appropriate buffer solutions and the fluorescence signal quantitated to give a precise measure of the increase or decrease in protein complex concentration in the presence of specific compounds. The optimal amount of multi-well plate washing is determined by the amount needed to obtain a low fluorescent background with the control "mutant zinc finger" that should not bind SWI/SNF while preserving a high fluorescent signal with another control containing a "wild type zinc finger" that should bind SWI/SNF with high affinity.

Compounds that significantly increase or decrease zinc finger-SWI/SNF interactions are further examined in in vitro chromatin remodeling and transcription assays and then tested in cultured cells to verify their efficacy before animal or human testing. It is also possible that a specific combination of compounds will be most efficacious. The ultimate goal is not only for efficacy, but for specificity, such that the compound or compound cocktail enhances or interferes with its target zinc finger-SWI/SNF subunit interaction without enhancing or interfering with the activity of other transcription factors. A non-comprehensive list of possible SWI/SNF subunits and zinc finger proteins include the following:

SWI/SNF Subunits:

BRG1, hBRM, BAF 155, BAF 170, INi1, BAF 60, BAF 47, BAF 57.

Zinc Finger Proteins:

1. GATA-1 (erythroid), Sp1 (ubiquitous), EKLF (erythroid), FKLF (fetal), BKLF (basic), GKLF (gut), LKLF (lung). Regulators of tissue-specific gene expression. GATA-1, EKLF, and FKLF.
2. All zinc finger-containing nuclear hormone receptors such as, androgen, estrogen, thyroid, progesterone, glucocorticoid receptors. Diseases such as prostate and breast cancers are initially treated by anti-androgen or -estrogen therapies but quickly progress to hormone-independent receptor status. This problem could be alleviated by treatment that prevents binding of hormone receptor to its target genes irrespective of hormone-responsiveness.
3. Wilm's tumor suppressor protein, WT1. WT1 encodes a zinc finger transcription factor implicated in kidney differentiation and tumorigenesis. It strongly regulates amphiregulin, a member of the epidermal growth factor family, among other genes.
4. BRCA1, 2 are implicated in hereditary breast and ovarian cancers.
5. KRAB repressor domain-containing zinc-finger proteins are involved in epigenetic silencing of genes.
6. BTB/POZ domain-containing zinc-finger proteins such as, PLZF (promyelocytic leukemia zinc finger), which is fused to RARalpha (retinoic acid receptor alpha) in a subset of acute promyelocytic leukemias (APLs), where it acts as a potent oncogene.

This assay can also be used to screen for drugs that modulate the interaction between SWI/SNF subunits and zinc finger peptides and/or fusion proteins containing zinc finger peptides. These peptides and proteins can potentially function as gene-specific transcriptional regulators when introduced into cells.

EXAMPLE 3

Activation of Repressed Genes by Facilitated Protein Binding Through Targeted Chromatin Remodeling by Zinc Finger Protein Motifs and SWI/SNF It has been demonstrated that zinc finger protein motifs can directly target SWI/SNF remodeling complexes to specific DNA sequences within chromatin. This results in structural changes that render the DNA region containing the specific target sequence accessible to interact with other regulatory proteins that cannot normally access their binding sites in chromatin. In this case, a chromatin-assembled HIV-1 promoter was in an "inactive structure" to which two of its regulatory proteins, NF-κB and TFE-3, could not bind and activate transcription from. Neither NF-κB nor TFE-3 function with SWI/SNF and, thus, cannot remodel chromatin or activate transcription even in the presence of this remodeling complex. However, by combining SWI/SNF with a zinc finger DNA-binding protein motif (or domain) that recognized a DNA sequence within the HIV-1 promoter, the SWI/SNF-zinc finger complex changed the closed chromatin structure of the promoter and enabled NF-κB and TFE-3 to interact with their DNA binding sites and activate transcription. In the absence of SWI/SNF, the zinc finger protein motif, NF-κB and TFE-3 had no effect on chromatin structure or transcription. In the absence of the zinc finger protein motif, SWI/SNF, NF-κB, and TFE-3 also had no effect on HIV-1 gene activation.

Thus, genes that are inactive due to the inability of their regulatory proteins to interact with their DNA binding sites in chromatin, can be activated by small protein domains (zinc fingers and other structures) that can direct or target chromatin remodeling or modifying complexes to specific DNA sequences. This provides a new therapeutic strategy to design small peptides that target a variety of chromatin remodeling or modifying (histone acetyltransferases, deacetylases, kinases, phosphatases, methylases, ubiquitinases) complexes to specific genes or regulatory regions to either activate or repress gene expression. This avoids the problems with introducing entire proteins or genes into cells by "gene therapy" techniques since small peptides can potentially be used.

EXAMPLE 4

Fetal-to-adult Hemoglobin Gene Switching by Specific Chromatin Remodeling Complexes and Transcription Factors β-thalessemias are common human blood disorders resulting from the aberrant inactivation of adult hemoglobin genes due to DNA mutation. These diseases become apparent after the normal silencing of the fetal globin genes before birth. Patients suffering from this disorder require blood transfusions for the remainder of their lives. If the fetal globin genes could be re-activated by reversing the developmentally programmed silencing, then normal fetal hemoglobin protein would be produced in adult patients and would functionally replace the adult form of this protein (encoded by the mutated adult globin gene). An assay was developed using chromatin-assembled recombinant DNA containing the human fetal and adult hemoglobin (β-globin) genes to identify protein complexes that function through chromatin to specifically regulate (activate or repress) either the fetal or adult genes. Using this assay, either the adult β-globin gene with SWI/SNF+EKLF or the fetal gamma-globin gene were differentially activated with a novel protein complex.

Thus, protein complexes (transcription factors, chromatin remodeling or modifying activities, or other proteins that regulate any cellular process through direct or indirect interaction with DNA in chromosomes) can be identified and functionally validated in this assay using individual genes, regulatory regions, or chromosomal domains. In addition to identifying specific activators of fetal or adult hemoglobin genes, a repressor of adult globin expression in fetal blood cells was also found. This is used as the target of a high-throughput drug screening assay to identify small molecule drugs or peptides that alleviate the symptoms of Cooley's anemia and other β-thalessemias and hemoglobinopathies.

EXAMPLE 5

Selective p53-dependent Regulation of Natural Target Genes Through Allosteric Interactions with Chromatin and Selective Recruitment of Co-factors p53 is a well-characterized tumor suppressor gene that is mutated in the majority of all human cancers. Interaction of p53 with variable DNA recognition sequences in a variety of genes controls distinct pathways of cell cycle arrest, DNA repair, and apoptosis in response to DNA damage. In vitro chromatin assays have been developed that reproduce p53-dependent activation of the p21 cell cycle inhibitor gene (which is normally upregulated in damaged cells but not in p53-defective cancer cells). Similar assays are also devised for genes that control apoptosis. These p53-dependent chromatin-based assays are adapted for high-throughput drug screening to identify compounds that alter the conformation of the most commonly mutated forms of p53 found in human cancers to increase its activity towards selective target genes. Because the DNA recognition sequences and structural topologies are so distinct among p53-regulated genes, only natural promoters will be used rather than artificial model genes or optimized DNA recognition sequences. These commonly used assays do not adequately represent the sophisticated nature of the p53 response and its ability to regulate distinct cellular pathways. p53 protein is quite sensitive to changes in its conformation and drugs that affect this equilibrium would be very beneficial in generating a functional p53 in many different types of cancer. The present assays take full advantage of the complexity of p53 regulation by assembling diverse p53 DNA binding sites into chromatin structures that reproduce allosteric transcriptional regulation (the ability of a protein to have distinct functions (activator, repressor, etc.) by adopting different structural conformations and/or interacting with different co-factors when bound to distinct DNA or chromatin sites). In addition, it has been demonstrated that the co-factors (activators or repressors) recruited by chromatin-bound p53 are different depending upon which specific DNA binding site p53 is occupying. Other proteins, such as nuclear hormone receptors, also regulate expression of different genes by allosterism.

Thus, drugs are developed to exploit the ability of proteins such as the tumor suppressor, p53, and nuclear hormone receptors to recognize their diverse array of DNA binding sites differently and adopt distinct structural conformations depending upon the promoter context, DNA structure (relaxed, supercoiled), or chromatin structure of the particular binding site. The chromatin-based assays reproduce allosteric regulation by p53 on distinct DNA binding sites in terms of conformation of bound protein, ability to recruit distinct co-factors, and requirements for specific chromatin remodeling or modifying complexes. These chromatin-based assays are adapted for high-throughput screening to identify small molecule drugs or peptides that enhance or interfere with protein interaction or co-factor recruitment at selective chromosomal binding sites rather than at every DNA sequence that is bound by the protein. In this way, drugs are developed that affect only certain genes rather than every target gene of a particular protein. These assays are also utilized with DNA containing genetic polymorphisms in order to identify drugs that are most effective for specific individuals or subsets of the population. This drug specificity is very beneficial in alleviating deleterious side effects associated with many current treatments for a wide variety of diseases.

All publications, patents and patent documents are incorporated by reference herein, as though individually incorporated by reference. The invention has been described with reference to various specific and preferred embodiments and techniques. However, it should be understood that many variations and modifications may be made while remaining within the scope of the invention.

REFERENCES

Articles

Armstrong, J. A., Bieker, J. J. & Emerson, B. M. A SWI/SNF-related chromatin remodeling complex, E-RC1, is required for tissue-specific transcriptional regulation by EKLF in vitro. *Cell* 95, 93–104 (1998).

Armstrong, J. A. & Emerson, B. M. Transcription of chromatin: these are complex times. *Curr. Opin. Genet. Dev.* 8, 165–172 (1998).

Ashraf S I, Ip Y T. Transcriptional control: repression by local chromatin modification. *Curr Biol.* 8(19):R683–6. (Sep. 24, 1998) Review Beerli R R, et al. Positive and negative regulation of endogenous genes by designed transcription factors. *Proc Natl Acad Sci USA* (Jan. 31, 2000)

Beerli R R, et al. Toward controlling gene expression at will: specific regulation of the erbB-2/HER-2 promoter by using polydactyl zinc finger proteins constructed from modular building blocks. *Proc Natl Acad Sci USA* 95(25): 14628–33 (Dec. 8, 1998).

Bieker J J, Ouyang L, Chen X. Transcriptional factors for specific globin genes. *Ann N Y Acad Sci.* 850:64–9. (Jun. 30, 1998) Review.

Bieker, J. J. & Southwood, C. M. The erythroid Kruppel-like factor transactivation domain is a critical component for cell-specific inducibility of a beta-globin promoter. *Mol. Cell. Biol.* 15, 852–860 (1995).

Biggar, S. R. & Crabtree, G. R. Continuous and widespread roles for the Swi-Snf complex in transcription. *EMBO J.* 18, 2254–2264 (1999).

Burns, L. G. & Peterson, C. L. The yeast SWI-SNF complex facilitates binding of a transcriptional activator to nucleosomal sites in vivo. *Mol. Cell. Biol.* 17, 4811–4819 (1997).

Cairns, B. R. et al., *Cell* 87: 1249 (1996).

Chandrasegaran S, Smith J. Chimeric restriction enzymes: what is next? *Biol Chem.* 380(7–8):841–8. (1999 July–August 1999) Review.

Cosma M. P., Tanaka T. & Nasmyth K. Ordered recruitment of transcription and chromatin remodeling factors to a cell cycle- and developmentally regulated promoter. *Cell* 97: 299–311 (1999).

Davie, J. R. *Curr. Opin. Genet. Dev.*, 8: 173 (1998).

Dimova, D., Nackerdien, Z., Furgeson, S., Eguchi, S. & Osley, M. A. A role for transcriptional repressors in targeting the yeast Swi/Snf complex. *Mol. Cell* 4, 75–83 (1999).

Dunaief, J. L. et al. The retinoblastoma protein and BRG1 form a complex and cooperate to induce cell cycle arrest. *Cell* 79, 119–130 (1994).

Forrester, W. C. et al., *Genes Dev* 4: 1637 (1990).

Fryer, C. J. & Archer, T. K. Chromatin remodeling by the glucocorticoid receptor requires the BRG1 complex. *Nature* 393, 88–91 (1998).

Georgel, P. T. et al., *EMBO J.* 16: 4717 (1997).

Hung, H. L., Lau, J., Kim, A. Y., Weiss, M. J. & Blobel, G. A. CREB-Binding protein acetylates hematopoietic transcription factor GATA-1 at functionally important sites. *Mol. Cell. Biol.* 19, 3496–3505 (1999).

Imbalzano, A. N., Kwon, H., Green, M. R. & Kingston, R. E. Facilitated binding of TATA-binding protein to nucleosomal DNA. *Nature* 370, 481–485 (1994).

Jacobs and Michaels, *New Biol.*, 2:583, (1990)

Jacobs, *EMBO J.*, 11:4507–4517, 1992.

Kadonaga, J. T. Eukaryotic transcription: an interlaced network of transcription factors and chromatin-modifying machines. *Cell* 92, 307–313 (1998).

Kim J S, Pabo C O. Transcriptional repression by zinc finger peptides. Exploring the potential for applications in gene therapy. *J Biol Chem* 272(47):29795–800 (Nov. 21, 1997).

Kingston, R. E. & Narlikar, G. J. ATP-dependent remodeling and acetylation as regulators of chromatin fluidity. *Genes Dev.* 13, 2339–2352 (1999).

Klug, A. Zinc finger peptides for the regulation of gene expression. *J. Mol. Biol.* 293:215–218 (1999).

Klug and Rhodes, *Trends Biochem. Sci.*, 12:464 (1987).

Kowenz-Leutz E. & Leutz A. A C/EBP beta isoform recruits the SWI/SNF complex to activate myeloid genes. *Mol Cell* 4:735–743 (1999).

Kwon, H., Imbalzano, A. N., Khavari, P. A., Kingston, R.E. & Green, M. R. Nucleosome disruption and enhancement of activator binding by a human SW1/SNF complex. *Nature* 370, 477–481(1994).

Laurent, B. C., Treitel, M. A. & Carlson, M. Functional interdependence of the yeast SNF2, SNF5, and SNF6 proteins in transcriptional activation. *Proc. Natl. Acad. Sci. USA* 88, 2687–2691 (1991).

Lee C. H., Murphy M. R., Lee J. S. & Chung J. H. Targeting a SWI/SNF-related chromatin remodeling complex to the beta-globin promoter in erythroid cells. *Proc Natl Acad Sci USA* 96:12311–12315 (1999).

Martinez-Balbas, M. A. et al., *Proc. Natl. Acad. Sci. USA* 95: 132 (1998).

Mizuguchi, G. et al., *Mol. Cell.* 1: 141 (1998).

Muchardt, C. & Yaniv, M. A human homologue of *Saccharomyces cerevisiae* SNF2/SWI2 and *Drosophila* brm genes potentiates transcriptional activation by the glucocorticoid receptor. *EMBO J.* 12, 4279–4290 (1993).

Neely, K. E. et al. Activation domain-mediated targeting of the SWI/SNF complex to promoters stimulates transcription from nucleosomal arrays. *Mol. Cell* 4, 649–655 (1999).

O'Neill, D. et al. Tissue-specific and developmental stage-specific DNA binding by a mammalian SWI/SNF complex associated with human fetal-to-adult globin gene switching. *Proc. Natl. Acad. Sci. USA* 96, 349–354 (1999).

Orphanides, G. et al., *Cell* 92: 105 (1998).

Ostlund Farrants A.-K., Blomquist, P., Kwon, H. & Wrange, O. Glucocorticoid receptor-glucocorticoid response element binding stimulates nucleosome disruption by the SWI/SNF complex. *Mol. Cell. Biol.* 17, 895–905 (1997).

Owen-Hughes, T. et al., *Science* 273: 513 (1996).

Paranjape, S. M. et al., *Annu. Rev. Biochem.*, 63: 265 (1994).

Pazin, M. J., Kamakaka, R. T. & Kadonaga, J. T. ATP-dependent nucleosome reconfiguration and transcriptional activation from preassembled chromatin templates. *Science* 266, 2007–2011 (1994).

Phelan, M. L., Sif, S., Narlikar, G. J. & Kingston, R. E. Reconstitution of a core chromatin remodeling complex from SWI/SNF subunits. *Mol. Cell* 3, 247–253 (1999).

Smith J, Berg J M, Chandrasegaran S. A detailed study of the substrate specificity of a chimeric restriction enzyme. *Genes Res.* 27(2):674–81 (Jan. 15, 1999).

Sudarsanam, P., Cao, Y., Wu, L., Laurent, B. C. & Winston, F. The nucleosome remodeling complex, Snf/Swi, is required for the maintenance of transcription in vivo and is partially redundant with the histone acetyltransferase, Gcn5. *EMBO J.* 18, 3101–3106 (1999).

Takatsuji H. Zinc-finger proteins: the classical zinc finger emerges in contemporary plant science. *Plant Mol Biol.* 39(6):1073–8. (1999 April ) Review.

Thiel G, Lietz M, Leichter M. Regulation of neuronal gene expression. Naturwissenschaften. 86(1):1–7. (1999 January ) Review.

Utley, R. T., Cote, J., Owen-Hughes, T. & Workman, J. L. SWI/SNF stimulates the formation of disparate activator-nucleosome complexes but is partially redundant with cooperative binding. *J. Biol. Chem.* 272, 12642–12649 (1997).

Utley, R. T. et al Transcriptional activators direct histone acetyltransferase complexes to nucleosomes. *Nature* 394, 498–502 (1998).

Wang B S, Pabo C O. Dimerization of zinc fingers mediated by peptides evolved in vitro from random sequences. *Proc Natl Acad Sci USA* 96(17):9568–73 (Aug. 17, 1999).

Wang, W. et al. Diversity and specialization of mammalian SWI/SNF complexes. *Genes Dev.* 10, 2117–2130 (1996a).

Wang, W. et al. Purification and biochemical heterogeneity of the mammalian SWI/SNF complex. *EMBO J.* 15, 5370–5382 (1996b).

Winston, F. & Carlson, M. Yeast SNF/SWI transcriptional activators and the SPT/SIN chromatin connection. *Trends Genet.* 8, 387–391 (1992).

Wong, J., Shi, Y.-B. & Wolffe, A. P. Determinants of chromatin disruption and transcriptional regulation instigated by the thyroid hormone receptor: hormone-regulated chromatin disruption is not sufficient for transcriptional activation. *EMBO* 16, 3158–3171 (1997).

Yoshinaga, S. K., Peterson, C. L., Herskowitz, I. & Yamamoto, K. R. Roles of SWI1, SWI2, and SWI3 proteins for transcriptional enhancement by steroid receptors. *Science* 258, 1598–604 (1992).

Yudkovsky, N., Logie, C., Hahn, S. & Peterson, C. L. Recruitment of the SWI/SNF chromatin remodeling complex by transcriptional activators. *Genes Dev.* 13, 2369–2374 (1999).

Zhao, K. et al. Rapid and phosphoinositol-dependent binding of the SWI/SNF-like BAF complex to chromatin after T lymphocyte receptor signaling. *Cell* 95, 625–636 (1998).

Books

Zinc-Finger Proteins in Oncogenesis: Dna-Binding and Gene Regulation (Annals of the New York Academy of Sciences, Vol 684) by Mel Sluyser (Editor) New York Academy of Sciences Transcription Factors and Human Disease (Oxford Monographs on Medical Genetics, No 37) Gregg L. Semenza (September 1998) Oxford Univ Press; ISBN: 0195112393

Eukaryotic Transcription Factors David S. Latchman 375 pages 3rd edition (May 1999) Academic Pr; ISBN: 0124371779

What is claimed is:

1. A method to identify a compound that modulates chromatin remodeling of a specific DNA sequence within chromatin comprising:
   a) providing chromatin assembled DNA containing a specific DNA sequence, which specific DNA sequence comprises a binding site for a zinc finger DNA binding domain of a nucleic acid regulatory protein, which zinc finger DNA binding domain interacts directly with a SWI/SNF chromatin remodeling complex comprising BRG1;
   b) contacting the chromatin assembled DNA with:
      1) the SWI/SNF chromatin remodeling complex comprising BRG1, and
      2) the nucleic acid regulatory protein zinc finger DNA binding domain alone;
      under conditions that permit the direct interaction of the SWI/SNF chromatin remodeling complex and the zinc finger DNA binding down; and
   c) determining the level of chromatin remodeling in the presence and absence of a test compound; wherein a difference in the level of chromatin remodeling in the presence and absence of the test compound identifies the test compound as a compound that modulates chromatin remodeling of the specific DNA sequence within chromatin.

2. The method of claim 1, wherein the specific DNA sequence is an individual gene or portion thereof, a regulatory region or a chromosomal region.

3. The method of claim 1, wherein the nucleic acid regulatory protein is a transcription factor.

4. The method of claim 1, wherein the SWI/SNF chromatin remodeling complex is E-RC1.

5. Theg method of claim 1, wherein the zinc finger DNA binding domain is from GATA-1, Sp1, EKLF, FKLF, BKLF, GKLF, LKLF, Wilm's tumor suppressor protein (WT1), BRCAI, BRCA2, KRAB, BTB/POZ, Zif268, GLI, Xfin, a BTB/POZ domain containing zinc finger protein, PLZF (promyelocytic leukemia zinc finger), or a nuclear hormone receptor.

6. The method of claim 1, wherein the zinc finger DNA binding domain is from a nuclear hormone receptor.

7. The method of claim 6, wherein the nuclear hormone receptor is selected from the group consisting of an androgen, estrogen, thyroid, progesterone, and glucocorticoid receptor.

8. The method of claim 1, wherein the zinc finger DNA binding domain binds to a promoter, an enhancer, an insulator, a silencer, or locus of control regions (LCRs).

9. The method of claim 1, wherein the test compound is a small molecule.

10. The method of claim 1, wherein the test compound is a peptide.

11. The method of claim 1, wherein the amount of chromatin remodeling is determined by assaying for DNAse hypersensitive sites within the specific DNA sequence.

12. The method of claim 1, wherein the zinc finger DNA binding domain is from GATA-1, Sp1, or EKLF.

13. The method of claim 1, wherein the zinc finger DNA binding domain is from GATA-1 or EKLF.

14. The method of claim 1, wherein the zinc finger DNA binding domain is from EKLF.

* * * * *